United States Patent [19]

Kozarich et al.

[11] Patent Number: 5,506,206
[45] Date of Patent: Apr. 9, 1996

[54] INCREASING BLOOD-BRAIN BARRIER PERMEABILITY WITH PERMEABILIZER PEPTIDES

[75] Inventors: John W. Kozarich, Cambridge; Gary F. Musso, Hopkinton; Bernard Malfroy-Camine, Arlington, all of Mass.

[73] Assignee: Alkermes, Inc., Cambridge, Mass.

[21] Appl. No.: 121,058

[22] Filed: Sep. 13, 1993

Related U.S. Application Data

[60] Division of Ser. No. 690,522, Apr. 23, 1991, Pat. No. 5,268,164, which is a continuation-in-part of Ser. No. 512,913, Apr. 23, 1990, Pat. No. 5,112,596.

[51] Int. Cl.$^6$ .............................. A61K 38/08; C07K 7/02
[52] U.S. Cl. .............................. 514/15; 530/314; 530/328
[58] Field of Search ............................. 514/15; 530/314, 530/328

[56] References Cited

U.S. PATENT DOCUMENTS

| | | |
|---|---|---|
| 4,709,010 | 11/1987 | Hölzemann et al. |
| 4,923,963 | 5/1990 | Stewart et al. |
| 5,112,596 | 5/1992 | Malfroy-Camine ........................ 424/2 |
| 5,162,497 | 11/1992 | Coy et al. |

FOREIGN PATENT DOCUMENTS

| | | |
|---|---|---|
| 1803492 | 6/1969 | Germany |
| 89/09231 | 10/1989 | WIPO |
| 91/16355 | 10/1991 | WIPO |

OTHER PUBLICATIONS

Kyle et al., "Design and Conformational Analysis of Several Highly Potent Bradykinin Receptor Antagonists," *J. Med. Chem.*, 34(3): 1230–1233 (1991).

Wahl, M., et al., "Effects of Bradykinin on Pial Arteries and Arterioles In Vitro and In Situ," *J. Cere. Blood Flow and Metab.*, 3(2): 231–237 (1983).

Unterberg, A. et al., "The Kallikrein–kinin System As Mediator in Vasogenic Brain Edema, Part I: Cerebral Exposure to Bradykinin and Plasma," *J. Neurosurg.*, 61: 87–96 (1984).

Unterberg, A. et al., "Effects of Bradykinin on Permeability and Diameter of Pial Vessels In Vivo," *J. Cere. Blood Flow and Metab.*, 4(4): 574–585 (1984).

Wahl, M. et al., "Cerebrovascular Effects of Bradykinin," *Neural Regulation of Brain Circulation*, C. Owman and J. E. Hardebo, eds., Elsevier Science Publ., pp. 419–430 (1986).

Olsen, S.-P. et al., "Substances that Rapidly Augment Ionic Conductance of Endothellum in Cerebral Venules," *Acta Physiol. Scand.*, 127: 233–241 (1986).

Wahl, M. et al., "Effects of Bradykinin on Cerebral Haemodynamics and Blood–Brain Barrier Function," In: Peptidergic Mechanisms in Cerebral Circulation (Edwinssen and McCulloch, Eds.) Chichester, Herwood, pp. 166–190 (1987).

Wahl, M. et al., "Mediators of Blood–Brain Barrier Dysfunction and Formation of Vasogenic Brain Edeme," *J. Cere. Blood Flow and Metab.*, 8: 621–634 (1988).

Raymond, J. J. et al., "Pharmacological Modification of Bradykinin Induced Breakdown of the Blood–Brain Barrier," *Can. J. Neuro. Sci.*, 13(3): 214–220 (Aug., 1986).

Saria, A. et al., "Vascular Protein Leakage in Various Tissues Induced by Substance P, Capsaicin, Bradykinin, Serotonin, Histamine and by Antigen Challenge," *Naunyn–Schniedeberg's Arch. Pharmacol.*, 324: 212–218 (1983).

Kamitani, T. et al., "Evidence for a Possible Role of the Brain Kallikrein–Kinin System in the Modulation of the Cerebral Circulation," *Circulation Research*, 57(4): 545–552 (Oct., 1985).

Schürer, L. et al., "Blood–Brain Barrier Permeability and Vascular Reactivity to Bradykinin After Pretreatment with Dexamethasone," *Acta Neuropathol.*, 77: 576–581 (1989).

Marceau, F. et al., "Pharmacology of Kinins: Their Relevance to Tissue Injury and Inflammation," *Gen. Pharmacol.*, 14(2): 209–229 (1983).

Hiesiger et al., "Opening the Blood–Brain and Blood–Tumor Barriers in Experimental Rat Brain Tumors: The Effect of Intracarotid Hyperosmolar Mannitol on Capillary Permeability and Blood Flow," *Annals Neurology*, 19(1): 50–59 (Jan., 1986).

Barry et al., "Amphotericin B and the Blood–Brain Barrier to Methotrexate," *Neurosurgery*, 10(2): 224–226 (Feb., 1982).

Williams, B. B., "Pharmacokinetics of Interferon in Blood, Cerebrospinal Fluid, and Brain after Administration of Modified Polyriboinosinic–Polyribocytidylic Acid and Amphotericin B," *J. Inf. Disease*, 146(6): 819–825 (Dec., 1982).

Ayre, S. G., "New Approaches to the Delivery of Drugs to the Brain," *Medical Hypotheses* 29: 283–291 (1989).

Unterberg, A. et al., "Blood Flow, Metabolism, and Function of the Brain During Cerebral Administration of Bradykinin," *Advances in Neurosurgery*, 13: 326–329, Dietz, H. et al. (Eds), Springer–Verlag Berlin Heidelberg (1985).

Rhaleb, N.-E. et al., "Structure–Activity Studies on Bradykinin and Related Peptides: Agonists," *Br. J. Pharmacol.*, 99(3): 445–448 (1990).

(List continued on next page.)

*Primary Examiner*—Christina Y. Chan
*Assistant Examiner*—Benet Prickril
*Attorney, Agent, or Firm*—Hamilton, Brook, Smith & Reynolds

[57] ABSTRACT

Polypeptides called receptor mediated permeabilizers (RMP) increase the permeability of the blood-brain barrier to molecules such as therapeutic agents or diagnostic agents. These receptor mediated permeabilizers are more efficacious than bradykinin in causing the blood-brain barrier to become more permeable. The permeabilizer A-7 or conformational analogues can be intravenously co-administered to a host together with molecules whose desired destination is the cerebrospinal fluid compartment of the brain. The permeabilizer A-7 or conformational analogues allow these molecules to penetrate the blood-brain barrier and arrive at this destination.

4 Claims, 11 Drawing Sheets

OTHER PUBLICATIONS

Chemical Abstracts, vol. 105 No. 19, 10 Nov. 1986, Columbus, OH, US; abstract No. 164987q.

Rhaleb, N.-E., Chem. Abst. 112(23); 211077z (1990).

Scarso, A. et al., "Synthesis and Biological Activities of Bradykinin Analogues with ψ(E,CH=CH) and ψ(CH$_2$—NH) Isosteric Peptide Bond Replacements," *Bull. Soc. Chim. Belg.* vol. 100, No. 5 pp. 381–399 (1991).

Stewart, "Chemical and Biologic Activity of Peptides Related to Bradykinin" *Handbook of Experimental Pharmacology,* vol. XXV Supplement, pp. 227–272 (1979).

Yamazaki et al., *Peptide Chemistry and Biology,* ed. Smith and Rivier, ESCOM, Leiden, pp. 154–156 (1992).

Regoli et al., "Pharmacology of Bradykinin and Related Kinins" *Pharmacology Rev.* 32(1), pp. 1–46 (1980).

Escher et al., "Biological Activities of Photoaffinity Labeling Analogues of Kinins and their Irreversible Effects on Kinin Receptors" *J. Med. Chem.* 24, pp. 1409–1413 (1981).

Vavrek et al., *Kinins IV (Adv. in Exp. Med. & Biol.),* vol. 198A, pp. 543–547 (1986).

INCREASING BLOOD-BRAIN BARRIER PERMEABILITY WITH PERMEABILIZER PEPTIDES

This application is a division of application Ser. No. 07/690,522, filed on Apr. 23, 1991 (now U.S. Pat. No. 5,268,164), which is a Continuation-in-Part of Ser. No. 07/512,913, filed Apr. 23, 1990 (U.S. Pat. No. 5,112,596), the teachings of which are incorporated herein by reference.

BACKGROUND

As our understanding of the nervous system and its related disorders increases, a wider range of therapeutic and diagnostic agents will become available. Once these agents have been identified, it will be necessary to deliver them to sites of diseased tissue in the central nervous system. Unfortunately, the existence of the blood-brain barrier limits the free passage of many types of molecules from the blood to cells of the central nervous system.

The physiological basis for the blood-brain barrier is the brain capillaries, which are comprised of endothelial cells (Goldstein, et al., *Scientific American*, 255: 74–83 (1986); Pardridge, W. M., *Endocrin. Rev.*, 7: 314–330 (1986)). These endothelial cells are different from those found in other tissues of the body. In particular, they form complex tight junctions between themselves. The actual blood-brain barrier is formed by these high-resistance tight intercellular junctions which form a continuous wall against the passive movement of many molecules from the blood to the brain. These cells are also different in that they have few pinocytotic vesicles, which in other tissues allow somewhat unselective transport across the capillary wall. In addition, continuous gaps or channels running through the cells, which would allow unrestrained passage, are absent.

One function of the blood-brain barrier is to protect the brain from fluctuations in blood chemistry. However, this isolation of the brain from the bloodstream is not complete. There does exist an exchange of nutrients and waste products. The presence of specific transport systems within the capillary endothelial cells assures that the brain receives, in a controlled manner, all of the compounds required for normal growth and function. The obstacle presented by the blood-brain barrier is that, in the process of protecting the brain, it excludes many potentially useful therapeutic and diagnostic agents.

There are several techniques that either physically break through the blood-brain barrier or circumvent it to deliver therapeutic or diagnostic agents. Among these are intrathecal injections, surgical implants, and osmotic techniques.

Intrathecal injection allows administration of agents directly into the brain ventricles and spinal fluid by puncturing the membranes surrounding the brain. Sustained delivery of agents directly into the spinal fluid can be attained by the use of infusion pumps that are implanted surgically. These spinal fluid delivery techniques are used to treat brain cancers, infections, inflammation and pain. However, they do not penetrate deeply into the brain.

Clinicians prefer to avoid intrathecal injections because they frequently are ineffective and can be dangerous. Substances injected intrathecally are distributed unevenly, slowly and incompletely in the brain. Since the volume of the spinal fluid is small, increases in intracerebral pressure can occur with repeated injections. Furthermore, improper needle or catheter placement can result in seizure, bleeding, encephalitis and a variety of other severe side effects.

An osmotic approach has been used by Dr. Edward Neuwelt at the University of Oregon to deliver chemotherapeutics and imaging antibodies to tumors in the brain. (Neuwelt, E. A., Implication of the Blood-Brain Barrier and its Manipulation, Vols 1 & 2, Plenum Press, N.Y. (1989)) This technique involves an arterial injection of a bolus of a hypertonic mannitol solution. The osmotic differential exerted by the mannitol causes the endothelial cells forming the barrier to shrink, opening gaps between them for a brief period. During this period, the drug is administered into the arterial system and is carried directly into the brain. The osmotic approach demonstrates that once past the barrier, therapeutic agents can be effectively distributed throughout the brain.

Because of the many risks involved, a 24- to 48-hour period in an intensive care unit is necessary following osmotic treatment. Mannitol can cause permanent damage (including blindness) to the eye. If the barrier is permeable for too long, brain edema results. Cells of the brain also can be damaged when neurotoxic substances in the blood, not generally accessible to the brain, are able to cross the barrier. Finally, there is a serious incidence of seizures in patients during and after the procedure.

SUMMARY OF THE INVENTION

The present invention pertains to compositions for increasing the permeability of the blood-brain barrier in an animal. These compositions are permeabilizers of the blood-brain barrier which are peptides having a core sequence of amino acids or amino acid analogues. In the core peptide, the sequence is arginine-proline-hydroxyproline-glycine-thienylalanine-serine-proline-(4-Me-tyrosine)-($CH_2NH$)arginine (SEQ. ID NO.: 1), from N-terminal to C-terminal, where $CH_2NH$ denotes a reduced peptide bond between the 4-Me-tyrosine and arginine amino acids. This peptide, which is an analogue of bradykinin, is referred to herein, for convenience, as permeabilizer A-7. Conformational analogues of this sequence are also compositions of this invention provided they have the property of increasing the permeability of the blood-brain barrier.

Pharmaceutical compositions that include permeabilizer A-7 or conformational analogues and a pharmaceutically acceptable carrier are also encompassed in this invention. These pharmaceutical compositions can also include the molecule for which the permeabilizer A-7 or conformational analogues make the blood-brain barrier more permeable.

Finally, the present invention pertains to a method for increasing the permeability of the blood-brain barrier of a host to a molecule contained in the host's bloodstream. This method comprises the administration of an effective amount of a permeabilizer A-7 or conformational analogues to the host. The molecule, for which the blood-brain barrier is made more permeable by the administered permeabilizer A-7 or conformational analogues, can also be co-administered with the permeabilizer A-7 or conformational analogues in this invention. Thus, the molecule to be delivered across the blood-brain barrier to the brain can be either an endogenous molecule residing in the bloodstream or an exogenous molecule that is co-administered sequentially or simultaneously with permeabilizer A-7 or conformational analogues.

An advantage of the present invention is that it provides a practical means for increasing the permeability of the blood-brain barrier by the administration of a permeabilizer A-7 or conformational analogues while co-administering a molecule of therapeutic, prophylactic or diagnostic value. For example, intravenous injection of permeabilizer A-7 or conformational analogues is significantly less invasive than intrathecal injection or osmotic disruption of the blood-brain barrier. The permeabilizer A-7 or conformational analogues preferentially increase the passage of lesser molecular weight substances.

The permeabilizer A-7 or conformational analogues of this invention can be administered by one of the traditional routes of administration. That is, the permeabilizer A-7 or conformational analogues can be administered by such techniques as intravascular, subcutaneous or intramuscular injections, oral, transdermal or intranasal administrations, and inhalation or sustained release routes. These routes of administration provide a variety of available options for delivering the permeabilizer A-7 or conformational analogues of this invention into the bloodstream of the host.

DETAILED DESCRIPTION OF THE INVENTION

Figure 1:
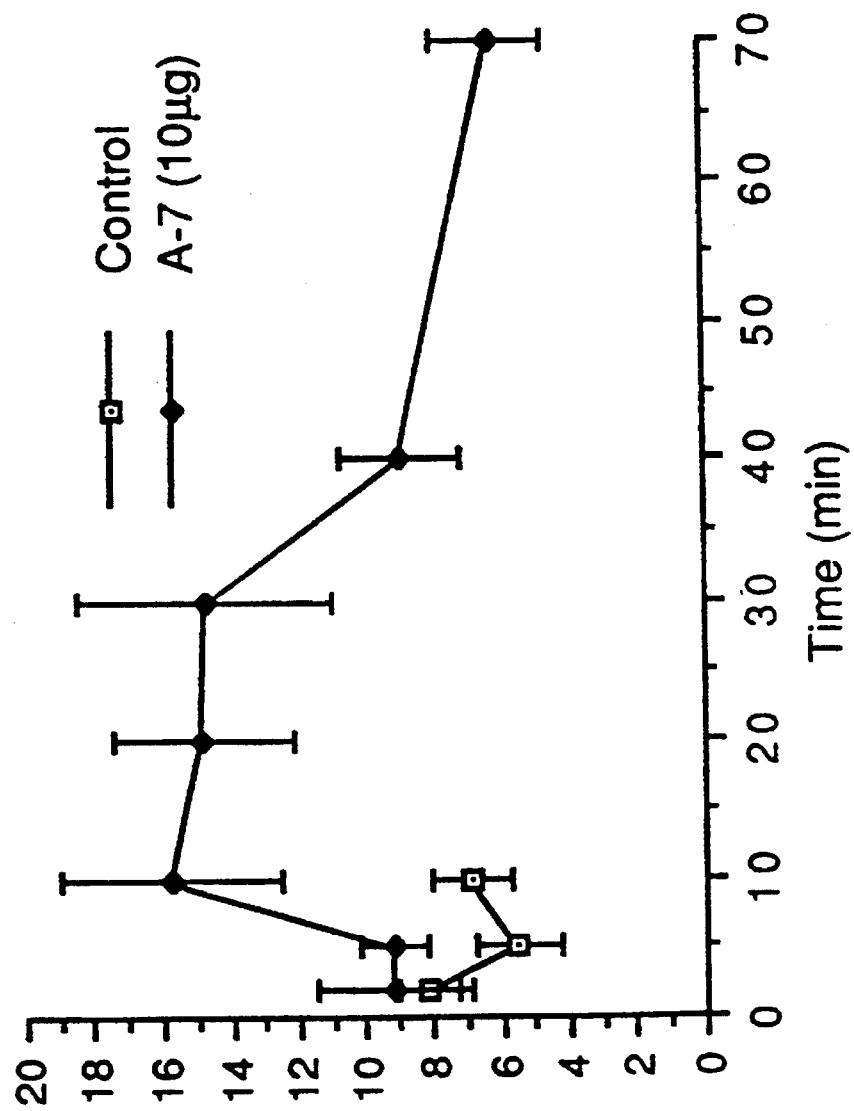
FIG. 1 is a graphic representation of the time course of brain uptake of sucrose after the administration of a specific amount of permeabilizer A-7 into different animals.

This invention pertains to compositions for increasing the permeability of the blood-brain barrier in an individual, such as a human being, to a molecule of interest. By increasing the permeability of the blood-brain barrier to the molecule of interest, the molecule more readily leaves the bloodstream and enters the interstitial fluid of the brain. There, it can interact with specific receptor molecules to produce a neuropharmaceutical effect or serve as a passive location marker. The increase in blood-brain barrier permeability to the molecule of interest provides accessibility of this molecule to the brain in higher relative concentrations than without the permeabilizer A-7 or conformational analogues while larger molecules in the bloodstream are less readily admitted.

The compositions of the invention are referred to as permeabilizer A-7 or conformational analogues. This term has been chosen to characterize the attribute of these substances for increasing the permeability of the blood-brain barrier to a molecule of interest. The increased permeability of the blood-brain barrier that occurs as a result of the administration of these compositions is believed to be mediated by receptor molecules, probably the $B_2$ receptors, located on the surface of brain endothelial cells that form the blood-brain barrier. The interaction between these receptors and the compositions of the invention apparently alters junctional or transportproperties between the cells thereby increasing the permeability of the blood-brain barrier to molecules such as the molecule of interest. These molecules more freely penetrate the blood-brain barrier as a result of this interaction at the receptors.

The substance known as bradykinin can also increase the permeability of the blood-brain barrier to molecules. This permeability increase probably occurs by the same mechanism as that for the permeabilizer A-7 or conformational analogues of this invention. That is, bradykinin probably interacts at the same receptors ($B_2$) as the permeabilizer A-7 or conformational analogues to cause an alteration of the blood-brain barrier permeability so that certain molecules can more easily leave the bloodstream to enter the interstitial fluid of the brain. For this reason, the permeabilizer A-7 or conformational analogues of this invention and bradykinin may be considered to be pharmacological agonists.

The permeabilizer A-7 or conformational analogues of this invention, like bradykinin, are peptides or peptidomimetics having a sequence of amino acids. This sequence of amino acids has such a conformation in aqueous solution that it can interact with molecules associated with the blood-brain barrier, e.g. receptor molecules, to effect an increase in the permeability of the blood-brain barrier to a molecule of interest that resides in or is injected into the bloodstream, The specific sequence of amino acids or mimetic replacements of the various permeabilizer A-7 or conformational analogues confers the proper conformation to them so they interact with the molecules associated with the blood-brain barrier to cause an increase in the permeability of the blood-brain barrier. If the primary sequence is improper, the substance will not adopt the proper conformation effecting an increase in the permeability of the blood-brain barrier.

The proper conformation that allows the permeabilizer A-7 or conformational analogues to interact with molecules to effect an increase in the permeability of the blood-brain barrier puts a restriction on the structure of the amino acids that compose the permeabilizer A-7 or conformational analogue sequence of this invention. Only particular sequences of amino acids and mimetics of these amino acids will fulfill the criterion for being a member of the permeabilizer A-7 or conformational analogues; namely, that they allow the proper conformation so they can effect an increase in the permeability of the blood-brain barrier.

A specific and preferred embodiment of this invention is the permeabilizer A-7 with the linear amino acid sequence from N-terminal to C-terminal of: arginine-proline-hydroxyproline-glycine-thienylalanine-serine-proline-(4-Me-tyrosine)ψ(CH$_2$NH)-arginine (SEQ. ID NO.: 1). This peptide is referred to herein as permeabilizer A-7. A method for synthesis of A-7 is given in the Examples. However, other known preparative methods can be employed to produce A-7 or conformational analogues.

This peptide, A-7, differs from a conventional linear sequence of amino acids in the following ways: the fifth amino acid is thienylalanine which is similar to phenylalanine but where a thienyl group has replaced the phenyl group; the eighth amino acid is tyrosine which has been substituted with a methyl group at the 4 position; and the peptide bond between the eighth and ninth amino acids has been replaced with a reduced peptide bond isostere, i.e. CH$_2$NH. Peptide and peptidomimetic analogues of this embodiment are also part of this invention provided they allow the proper conformation in aqueous solution so they effect an increase in permeability of the blood-brain barrier to molecules of interest. These compositions are termed "conformational analogues" of this embodiment.

This permeabilizer A-7 or conformational analogues may be compared to bradykinin which has the following linear amino acid sequence: arginine-proline-proline-glycine-phenylalanine-serine-proline-phenylalanine-arginine (SEQ. ID NO.: 2) (Lehninger, A. L., Biochemistry, p. 75 (1975)). The preferred permeabilizer A-7 or conformational analogues differs from bradykinin in the following respects: at the third amino acid, hydroxyproline replaces proline; at the fifth amino acid, thienylalanine replaces phenylalanine; at the eighth amino acid, 4-Me-tyrosine replaces phenylalanine; and between the eighth and ninth amino acids, a reduced peptide bond replaces a conventional peptide bond. These differences make the preferred permeabilizer A-7 more effective for increasing the permeability of the blood-brain barrier when compared to bradykinin. Much less of the permeabilizer A-7 is required to increase the blood-brain barrier permeability and more of the molecule of interest crosses the blood-brain barrier at a given administered amount of the permeabilizer A-7 when compared to the same administered amount of bradykinin.

Characteristic features of the permeabilizer A-7 or conformational analogues of this invention are important for the permeabilizer A-7 or conformational analogues to allow the proper conformation to effect an increase in the permeability of the blood-brain barrier to a molecule of interest. The following modifications can be made to A-7, yet retain the proper conformation: the N-terminal arginine is replaced by an amino acid analogue containing a guanidino side chain;) the second amino acid (proline) is replaced by hydroxyproline, dehydroproline, N-methylalanine or another proline analogue; the third amino acid (hydroxyproline) is replaced by proline, dehydroproline, another proline analogue, alanine, sarcosine or N-methylalanine; the fifth amino acid (thienylalanine) is replaced by another aromatic amino acid or a hydrophobic aliphatic amino acid; the sixth amino acid (serine) is replaced by glycine, threonine, alanine, allothreonine, asparagine, glutamine or analogues thereof; the seventh amino acid (proline) is replaced by hydroxyproline, dehydroproline, N-methylalanine or another proline analogue; the eighth amino acid (4-Me-tyrosine) is replaced by another O-alkyl tyrosine or a hydrophobic aliphatic amino acid; and the C-terminal arginine is replaced by an amino acid analogue containing a guanidino side chain; and the peptidomimetic isosteric bond between the eighth amino acid (4-Me-tyrosine) and the C-terminal arginine (ψ(CH$_2$NH)) is replaced by ψ(CSNH), ψ(NHCO) or ψ(CH$_2$S).

Within this general scheme for obtaining conformational analogues of A-7, it is preferred that the changes be limited to: β-cycloarginine, homoarginine, γ-hydroxyarginine, canavanine, N$^\omega$-amidinocitrulline, 2-amino-4-guanidobutanoic acid, citrulline or homocitrulline for the N-terminal or C-terminal arginine; hydroxyproline or dehydroproline for the second or seventh amino acids (proline); proline or dehydroproline for the third amino acid (hydroxyproline); dehydrophenylalanine, phenylalanine or another aromatic analogue for the fifth amino acid (thienylalanine); glycine or threonine for the sixth amino acid (serine); and O-alkyl tyrosine for the eighth amino acid (4-Me-tyrosine).

With these specified amino acid designations, the proper conformation of the permeabilizer A-7 or conformational analogues is achieved so that the permeabilizer A-7 or conformational analogues can effect an increase in the permeability of the blood-brain barrier to a molecule of interest. These amino acid positions and designations appear to be important for the permeabilizer A-7 or conformational analogues to allow the proper conformation so that the desired interaction can occur.

Another variation that is within this invention is the optional addition of one or more amino acids or analogues to the N-terminal arginine or the masking of the primary amino group of this arginine (e.g. acetylation). These additional amino acids are linked by typical peptide bonds to each other and to the N-terminal arginine, thus making the additional amino acids the N-terminal region of the permeabilizer A-7 or conformational analogues polypeptide. These additional amino acids are arginine or lysine or, if there are two additional amino acids, the N-terminal amino acid can be methionine. If a single amino acid is added and is arginine, it can be substituted with an acetyl or other masking agents (e.g. propyl, benzene, etc.) again or be the L-isomeric form. Preferred additional N-terminal amino acid groups are -arginine-, acetyl arginine-, lysine-, arginine-arginine-lysine-lysine-, methionine-arginine- or methionine-lysine, where these additional amino acids are of either D or L configuration.

The amino acids that constitute the core sequence of the permeabilizer A-7 or conformational analogues of this invention should be formed as the L-isomer. If the D-isomer is substituted for one or more of the core constituent amino acids of the sequence, particularly in the C-terminal region, the increase in permeability of the blood-brain barrier is often severely attenuated, when the resulting permeabilizer A-7 or conformational analogues is administered to the host animal.

This invention also pertains to pharmaceutical compositions suitable for administration to host animals to increase the permeability of the blood-brain barrier to a molecule of interest. These pharmaceutical compositions contain one or more of the permeabilizer A-7 or conformational analogues in a pharmaceutically acceptable carrier known to one of skill in the art. The pharmaceutical composition will often be given by injection into a blood vessel of the host animal. In particular, the pharmaceutical composition can be intravenously injected since the permeabilizer A-7 or conformational analogues is not significantly degraded by angiotensin converting enzyme (ACE) known to be present in high concentrations in the lung. By contrast, bradykinin is significantly degraded by ACE.

The quantity of permeabilizer A-7 or conformational analogues to be administered, and therefore packaged as units of the pharmaceutical composition, depends upon the efficacy of the chosen permeabilizer A-7 or conformational analogues, the size and other individual variations of the host compared to the population of hosts as a whole and the molecule of interest to be passed through the blood-brain barrier. The actual amounts and concentrations of permeabilizer A-7 or conformational analogues in the pharmaceutical compositions can be readily ascertained by a person of skill in the art.

The pharmaceutical compositions of this invention can also contain the molecule of interest to be passed across the blood-brain barrier. In these compositions, both the molecule of interest and the permeabilizer A-7 or conformational analogues that fosters its penetration of the blood-brain barrier are included in a convenient package. This allows the two substances to be co-administered so the efficiency of administration of these substances is maximized.

This invention also relates to a method for increasing the permeability of the blood-brain barrier of a host to a molecule present in the host's bloodstream. The host can be any animal which possesses a central nervous system (i.e., a brain). Examples of hosts include mammals, such as humans, domestic animals (e.g, dog, cat, cow or horse) and animals intended for experimental purposes (e.g., mice, rats, rabbits).

The amount of A-7 or conformational analogue administered to a host that is efficacious for increasing the permeability of the blood-brain barrier is well below the toxic level for that host. Thus, nontoxic dosages of A-7 or conformational analogues can be administered without sacrificing permeabilizing activity.

The molecule in the host's bloodstream can be exogenous to the host. For example, it can be a neuropharmaceutical agent which has a therapeutic or prophylactic effect on a neurological disorder. Examples of neurological disorders include cancer (e.g., brain tumors), Autoimmune Deficiency Syndrome (AIDS), epilepsy, Parkinson's disease, multiple sclerosis, neurodegenerative disease, trauma, depression, Alzheimer's disease, migraine, pain, or a seizure disorder.

Classes of neuropharmaceutical agents which can be used in this invention include antimicrobial agents, antiparasitic agents, agents that act on the autonomic nervous system including adrenergic agents and catecholaminergic agents, anticonvulsants, nucleotide analogues, antineoplastic agents, anti-trauma agents, excitatory amino acids and other classes of agents used to treat or prevent a neurological disorder. Examples of antibiotics include amphotericin B, gentamicin sulfate, pyrimethamine and penicillin. An example of an adrenergic agent (including blockers) is atenolol. Examples of catecholaminergic agents include dopamine, diacetyldopamine and domperidone. Examples of antineoplastic agents include adriamycin, methotrexate, cyclophosphamide, etoposide, carboplatin and cisplatin. An example of an anticonvulsant which can be used is valproate. Examples of anti-trauma agents which can be used include calpain inhibitors, channel blockers, glutamate chelators and oxygen radical scavengers. Nucleotide analogues which can be used include azido thymidine (AZT), dideoxy Inosine (ddI) and dideoxy cytidine (ddC).

The molecules in the host's bloodstream can also be diagnostic imaging or contrast agents. Examples of diagnostic agents include substances that are labelled with radioactivity, such as 99m-Tc glucoheptonate, or substances used in Magnetic Resonance Imaging (MRI) procedures such as Gadolinium doped chelation agents (e.g. Gd-DTPA-).

The route of administration of exogenous molecules to the host's bloodstream can be parenterally by subcutaneous, intravascular, preferably intravenous, or intramuscular injection or by absorption through a bodily tissue, such as the digestive tract, the respiratory system or the skin. The form in which the molecule is administered (e.g., capsule, tablet, solution, emulsion) will depend, at least in part, on the route by which it is administered.

The administration of the exogenous molecule to the host's bloodstream and the intravenous injection of the chosen permeabilizer A-7 or conformational analogues can occur simultaneously or sequentially in time. For example, a therapeutic drug can be administered orally in tablet form while the intravenous administration of the permeabilizer A-7 or conformational analogues is given later (e.g. 30 minutes). This is to allow time for the drug to be absorbed in the gastrointestinal tract and taken up by the bloodstream before the permeabilizer A-7 or conformational analogues is given to increase the permeability of the blood-brain barrier to the drug. On the other hand, the permeabilizer A-7 or conformational analogues can be administered before or at the same time as an intravenous injection of a drug. Thus, the term "co-administration" is used herein to mean that the permeabilizer A-7 or conformational analogues and the exogenous molecule will be administered at times that will achieve significant concentrations in the blood for producing the simultaneous effects of increasing the permeability of the blood-brain barrier to the exogenous molecule and allowing the maximum passage of the exogenous molecule from the blood to the interstitial fluid of the central nervous system.

In addition, the molecule to be delivered to the brain via the host's bloodstream can be endogenous to the host. That is, it can be a biological product that is naturally synthesized and produced by the host. Examples of such biological products include sugars, such as glucose, and small peptides, such as enkephalins and thyroid stimulating hormone releasing factor.

An effective amount of the permeabilizer A-7 or conformational analogues is that amount which will significantly increase the blood-brain barrier permeability for the molecule of interest. In other words, it will increase the permeability of the blood-brain barrier to allow sufficient quantities of a molecule of interest to pass from the blood to the interstitial fluid of the brain to exert a therapeutic or prophylactic effect or allow diagnostic procedures. The effective amount will be determined on an individual basis and will be based, at least in part, on consideration of the individual's size, the specific disease, the severity of symptoms to be treated, the result sought, the specific permeabilizer A-7 or conformational analogues, and other variations among hosts, etc. Thus, the effective amount can be determined by one of ordinary skill in the art employing such factors and using no more than routine experimentation.

The increase in permeability of the blood-brain barrier in response to the permeabilizer A-7 or conformational analogues relates not only to the quantity of molecules passing from the blood to the brain, but also, to the type of molecule of interest. The effect of the permeabilizer A-7 or conformational analogues is to preferentially increase the passage of small molecular weight substances through the blood-brain barrier.

The invention is further illustrated by the following specific examples.

EXAMPLE I

Synthesis of Boc-4-MeTyrψ(CH$_2$N(Z)Arg (Tos)-O-Resin

N-BOC-O-Methyl-L-Tyrosine N-Methoxy-N-Methylamide

To 350 ml of anhydrous THF on ice was added 3.635 g (37.2 mmols) of N,O-dimethylhydroxylamine hydrochloride. The mixture was stirred for 10 minutes to allow most of the N,O-dimethylhydroxylamine hydrochloride to dissolve. Then, the following ingredients were successively added to the flask: 10 g (33.8 mmols) of N-Boc-O-methyl-L-tyrosine, 6.977 g (33.8 mmols) of dicyclohexylcarbodiimide, 1.96 g (16.04 mmols) of 4-dimethylaminopyridine, and 6.209ml (35.64 mmols) of N,N-diisopropylethylamine. When all of the reagents had been added, the reaction flask was placed in a cold room (4° C.) and stirred for 12 hours. The contents of the flask were gravity filtered using Whatman Qualitative #1 filter paper. The filtrate was concentrated by means of a rotary evaporator to viscous oil which was then redissolved in 200 mls of methylene chloride. This crude reaction mix was allowed to sit at 4° C. for one hour and then filtered as before in order to remove any residual dicyclohexylurea. The filtrate was again concentrated by means of a rotary evaporator and redissolved in 50 ml of methylene chloride in preparation for column chromatography. Column chromatography was performed using silica (230–400 mesh, 60A) as the adsorbent and 50/50 ethyl acetate/hexane as the eluent. The column used for this scale reaction was 70 cm in length and 10 cm in diameter. The product eluted after approximately 400 ml of eluent had been run through the column. The fractions were all checked by TLC using Silica Gel 60 F-254 glass backed plates. The desired product (Rf value of 0.46) was pooled and concentrated in vacuo. Concentration afforded clear, colorless oil which was placed under high vacuum for several hours. At the end of this time the product remained as a semi-solid material and with time became completely solid.

There remained 5.73 g (50.2%) of a white solid with amp of 58°–62° C.; IR (cm$^{-1}$, KBr) 3320, 2980, 2840, 1710, 1655, 1520, 1205, 1180; MS m1e 338.4 (M+); $^1$H (CDCl$_3$, 300 MHz) δ7.08 (d 2H J=8.50 Hz), δ6.82 (d, 2H, J=8.50 Hz), δ5.15 (br d, 1H, J=8.90 Hz), δ4.89 (br m, 1H), δ3.78 (s, 3H), δ3.66 (s, 3H), δ3.17 (br s, 3H), δ2.99 (d of d, 1H, J=6.0 Hz), δ2.83 (d of d, 1H, J=6.0 Hz), δ1.39 (s, 9H); Anal. Calcd; C, 60.35; H, 7.69; N, 8.28. Found: C, 60.58; H, 8.02; N, 8.31.

N-(t-Butyoxycarbonyl)-O-Methoxy-L-Tyrosinal

To 150 ml of anhydrous ethyl ether was added 1.04 g (27.37) mmols) of lithium aluminum hydride and the suspension was gently refluxed for 30 minutes. Upon cooling to 4° C., the reflux condenser was replaced by a pressure equalizing dropping funnel containing 7.4 g (21.9 mmols) of N-(t-butoxycarbonyl)-O-methyl-L-tyrosine N-methoxy-N-methylamide dissolved in 100 ml of anhydrous ethyl ether. The contents of the funnel were added over one hour. The reaction mix was allowed to react for an additional two hours. At the end of this time a cold solution of KHSO$_4$ (5.433 g in 230 ml of H$_2$O) was added to the reaction vessel. The layers were separated and the aqueous layer was extracted three times with 150 mls of ether each time. The ether layers were combined and worked up as follows. Washed three times with 200 mls of 3N HCl. Washed three times with 200 mls of saturated sodium bicarbonate. Washed three times with 200 mls of brine. Dried over magnesium sulfate, filtered , and concentrated in vacuo. There remained 3.78 g (61.6%) of a white solid with amp of 69°–72° C.: Rf=0.65 in 50/50 ethyl acetate/hexane; IR (cm$^{-1}$, KBr) 3360, 2840, 1740, 1695, 1530, 1255, 1180: MS m/e 279.3 (M+); $^1$H (CDCl$_3$), 300 MHz) δ9.63 (s, 1H), δ7.08 (d, 2H, J=8.5 Hz) δ6.84 (d, 2H, J=8.5), δ5.05 (br s, 1H), δ4.40 (m, 1H), δ3.79 (s, 3H), δ3.06 (d, 2H, J=6.50), δ1.44 (s, 9H); $^{13}$C NMR (CDCl$_3$, 75.47 MHz) δ200, 158.79, 130.28, 127.69, 114.27, 61.05, 55.29, 34.70, 28.26; Anal. Calcd: C, 64.51; H, 7.52; N, 5.01. Found: C,64.60, H, 7.86; N, 4.93.

N-BOC-(4-MeTyr)ψ(CH$_2$NH)Arg(Tos)-OH

To a flask containing 100 ml of Methanol:Acetic Acid (99:1) was added 4.92 g (15 mmols) of N$^g$-Tosyl-arginine followed by 1.15 g (18 mmol) of sodium cyanoborohydride. The reagents were stirred for 5 minutes followed by the addition of 4.46 g of N-BOC-4-Me-Tyrosinal. After 30 minutes, an additional 1.15 g (18 mmols) of sodium cyanoborohydride was added to the reaction vessel. Three additional portions of sodium cyanoborohydride were added at thirty minute intervals and the reaction was allowed to stir overnight. The reaction was worked-up by evaporating the solvent. The residue was dissolved in heptane and dried followed by dissolution in ether and drying. Water (200 ml) was added to the flask and the solid collected by filtration. TLC analysis revealed a homogenous product with an Rf of 0.3 in CHCL3:MeOH,4:1). NMR was consistent with the expected product.

N-BOC-(4MeTyr)ψ(CH$_2$N[Z])Arg(Tos)-OH

To 2.14 g (3.61 mmole) of the pseudodipeptide above was added 1.65 g (19.6 mmole) of NaHCO$_3$ in 100 ml of 1:1 dioxane/water. Benzyl chloroformate (0.6 ml, 4 mmol) was added and the reaction was stirred overnight. The solvents were removed in vacuo leaving a gummy residue. The residue was suspended in 100 ml of water and this was acidified to pH2 with HCl and extracted three times with ethyl acetate. The combined ethyl acetate fractions were dried over magnesium sulfate, filtered and evaporated to provide 2.35 g (90%) of the desired material as a crude amorphous white solid. Recrystallization from methylene chloride/hexane provided 2.18 g (83%) of the product as a white solid. TLC analysis revealed a homogeneous product with an Rf of 0.64 in (CHCl$_3$; MeOH, 4:1).

Attachment of the Protected Pseudodipeptide to the Polystyrene Resin

The protected pseudodipeptide was attached to hydroxymethyl resin (Polystyrene-1% Divinylbenzene, 0.7 mequiv./g) using dicyclohexylcarbodiimide and 4-dimethylaminopyridine. To 1.87 g of hydroxymethyl resin (1.31 mmol) was added 2.28 g (3.28 mmol) of the protected pseudodipeptide, 410 mg (3.33 mmol) of 4-dimethylaminopyridine, and 25 ml of anhydrous dimethylformamide in a 50 ml polypropylene tube. To this was added 680 mg (3.3 mmol) of dicyclohexylcarbodiimide and the vessel was shaken overnight at room temperature. The resin was collected by filtration and washed successively three times each with methylene chloride and methanol and dried overnight in vacuo to provide 2.6 g of resin. Substitution by weight gain was calculated to be 0.54 mmol/g.

EXAMPLE II

Synthesis and Purification of A-7

A-7 was prepared by solid-phase peptide synthesis by sequentially assembling the remaining amino acids (in a C- to N-fashion) onto the resin bound protected pseudodipeptide. The peptide was synthesized on a Beckman 990 peptide synthesizer using the following program for each coupling cycle, 1—Wash, $CH_2Cl_2$ (3×1 min); 2—Deprotect 40% $TFA/CH_2Cl_2$ (2×10 minutes); 3—Wash, $CH_2Cl_2$ (3×1 min); 4—Wash. Isopropanol (2×1 min); 5—Wash, $CH_2Cl_2$ (3×1 min); 6—Neutralize 5% $DIEA/CH_2Cl_2$ (3×2 min); 7—Wash, $CH_2Cl_2$ (5×1 min); 8—Couple (3 equivalents Boc-Amino acid, 3 equivalents of BOP) 1×60 min; 9—Wash, $CH_2Cl_2$ (3×1 min); 10—Wash, Isopropanol (2×1 min); 11—Wash, $CH_2Cl_2$ (3×1 min); 12- Test for coupling by ninhydrin. If recoupling was necessary as judged by a positive ninhydrin test, a partial cycle starting at step 6 to the end was done. Following assembly of the complete protected peptide, the N-terminal BOC group was removed by using steps 1–5 in the cycle and the resin dried.

The crude peptide was isolated from the resin by treatment of the protected peptide-resin with anhydrous HF containing 10% anisole for 1 hour at 0° C. The HF was removed in vacuo and the crude resin/peptide was washed with ether three times. The peptide was extracted with 10% acetic acid and lyophilized to yield a crude peptide.

The peptide was partially purified by HPLC using a 0.1% TFA/acetonitrile gradient (10–40% over 30 minutes) on a $C_{18}$ reverse phase support. The peptide was further purified using isocratic 15% acetonitrile in 0.1% TFA as an eluant on a $C_{18}$ support. The fractions from the main peak were combined to provide purified A-7 which appeared homogeneous by TLC, Electrophoresis, and HPLC. FAB/MS analysis yielded the expected MW of 1098. Amino acid analysis after 6N HCl hydrolysis (24 hours at 110° C.) gave the following composition: (Ser(1)0.89, Pro (2)2.00, Gly (1)0.97, Arg (1)1.03, Thi(1)0.73.4Me-Tyr-$\psi(CH_2NH)$-Arg(1) was detected by an alternate method, but was partially destroyed in hydrolysis.

EXAMPLE III

Time Course of Blood-Brain Barrier Opening in Mice and Rats

Female Balb/C mice weighing approximately 20 g were used. All solutions were prepared in sterile phosphate-buffered saline. An intravenous A-7 injection of 10 μg/100 μl was given in the tail vein at time=0. At various specified times following this, an injection of $^{14}C$-sucrose (3×10$^6$ dpm) was also made in the tail vein. Two, five or ten minutes later, the mice were killed. Blood was collected in heparinized tubes and centrifuged to separate plasma from the resulting pellet. A 100 μl aliquot of plasma was counted by liquid scintillation counting after the addition of 15 ml of Aquasol-2 (Dupont). The brain was removed and homogenized in 2.5 ml of water and 2.5 ml of 1% sodium dodecyl sulfate (SDS). One ml of the homogenate was aliquoted and added to 15 ml of Aquasol-2 for counting. Brain uptake of sucrose was calculated and expressed as percent of injected dose×100. As seen in FIG. 1, the uptake of $^{14}C$-sucrose at 10 and 20 minutes was significantly higher in the presence of A-7. The blood-brain barrier remained permeable to sucrose for at least 20 minutes following injection of A-7 but did not remain open after 40 minutes. Each data point represents the mean±s.d. from 8 mice.

A similar protocol was followed using female Harlan Sprague-Dawley rats (150–200 g). Each animal received a bolus injection of 100 μg A-7 at time zero. Either immediately or at 2, 5, 10, 20, 30 or 60 minutes after the A-7 injection, $^{14}C$ sucrose was intravenously injected and the rats were sacrificed either 2 or 5 minutes later for the early time points or 10 minutes later for time points of 10 minutes or longer.

Figure 2:
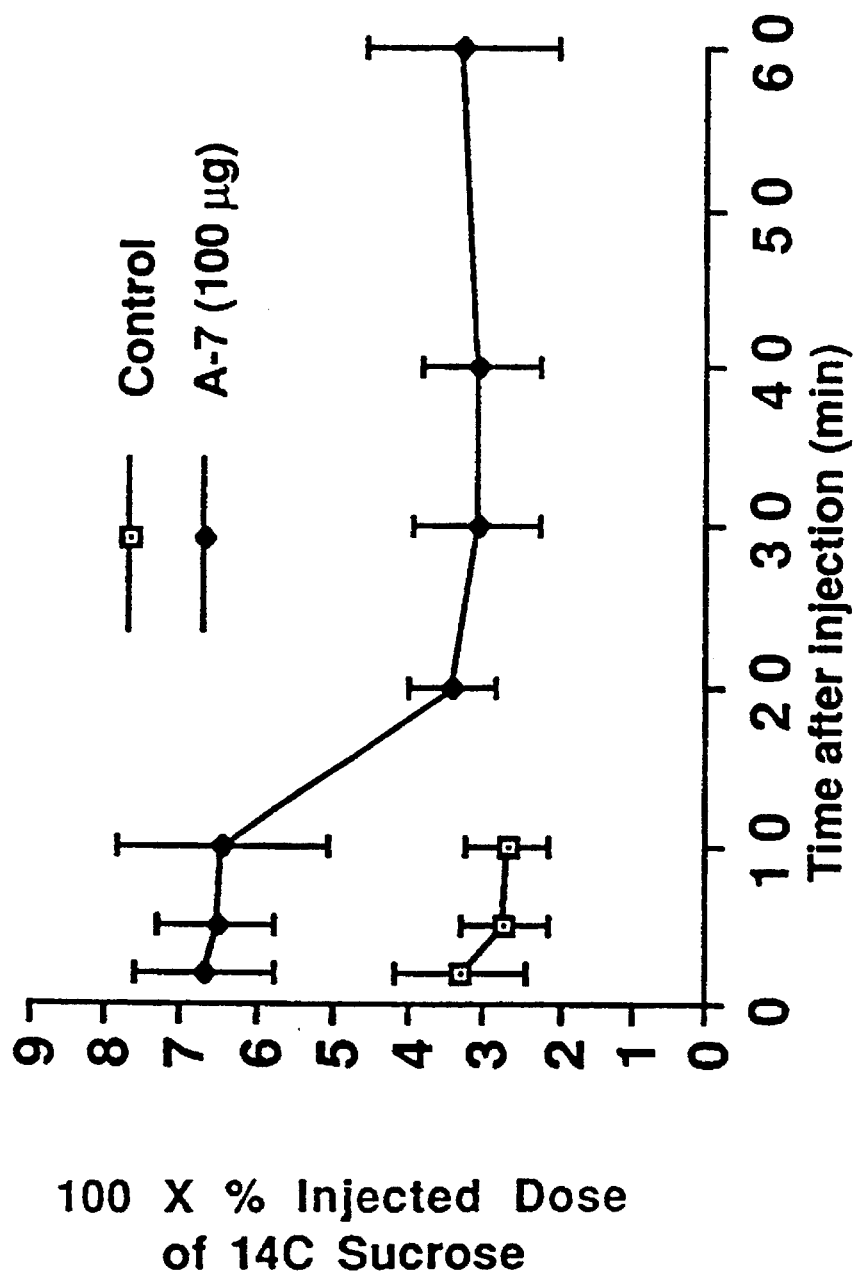
FIG. 2 is a graphic representation of the time course of brain uptake of sucrose after the administration of a specific amount (100 μg) of a permeabilizer A-7.

The results, generated from 5–12 rats at each time point, are shown in FIG. 2. Again, brain uptake of sucrose was calculated and expressed as percent of injected dose×100. The control uptake represents the amount of $^{14}C$ sucrose taken up by the brain at 2, 5 or 10 minutes for rats that received no A-7. These data indicate that the duration of increased permeability after a single bolus injection of A-7 is less than 20 minutes in rats.

In some experiments whole blood samples and intact brain tissue were combusted in a Packard Model 307 Oxidizer and the radioactivity collected and counted in a liquid scintillation counter. The results obtained by either homogenization or combustion of samples were equivalent.

EXAMPLE IV

Figure 3A:
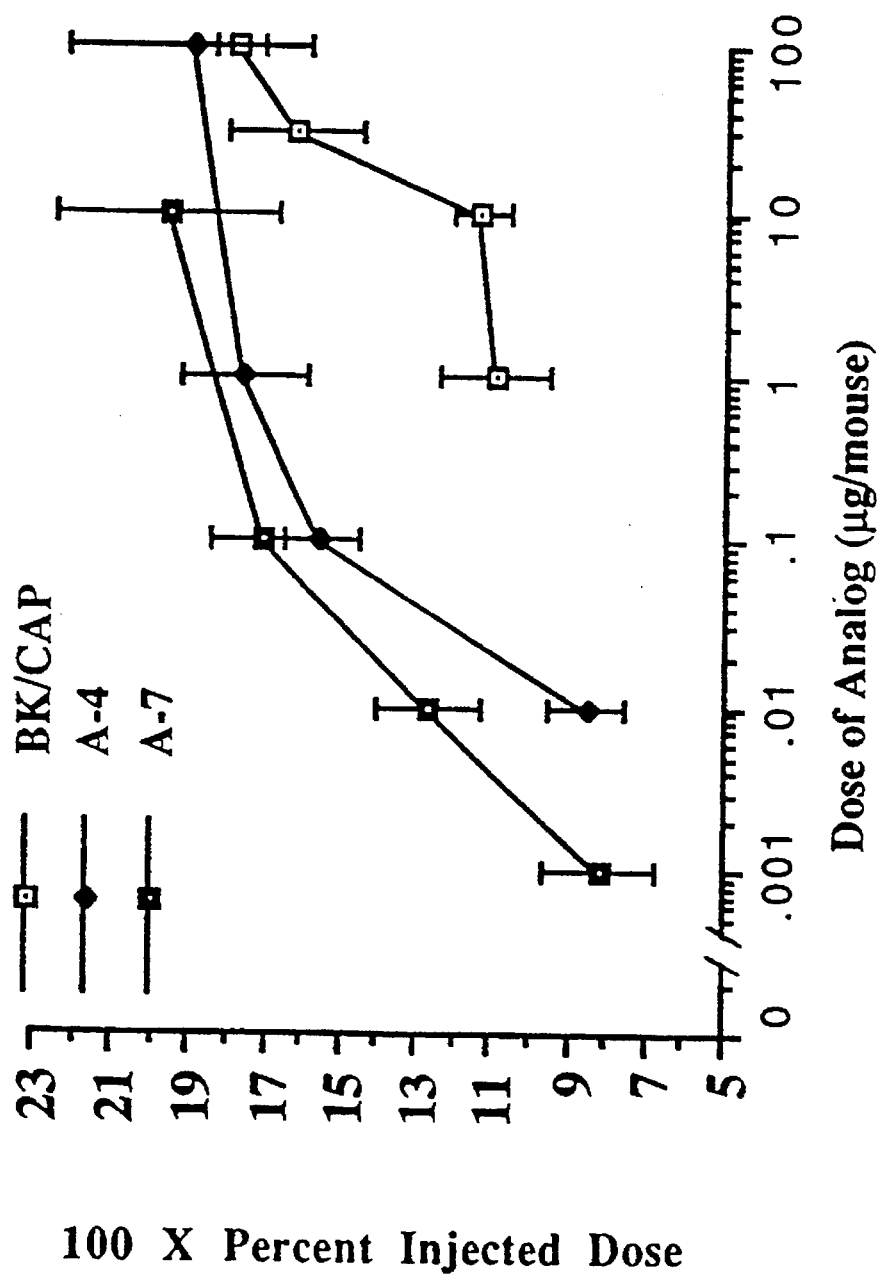
FIG. 3a is a graphic representation of brain uptake of sucrose, displayed as percent of injected dose, following the administration of permeabilizer or bradykinin analogues.
Figure 3B:
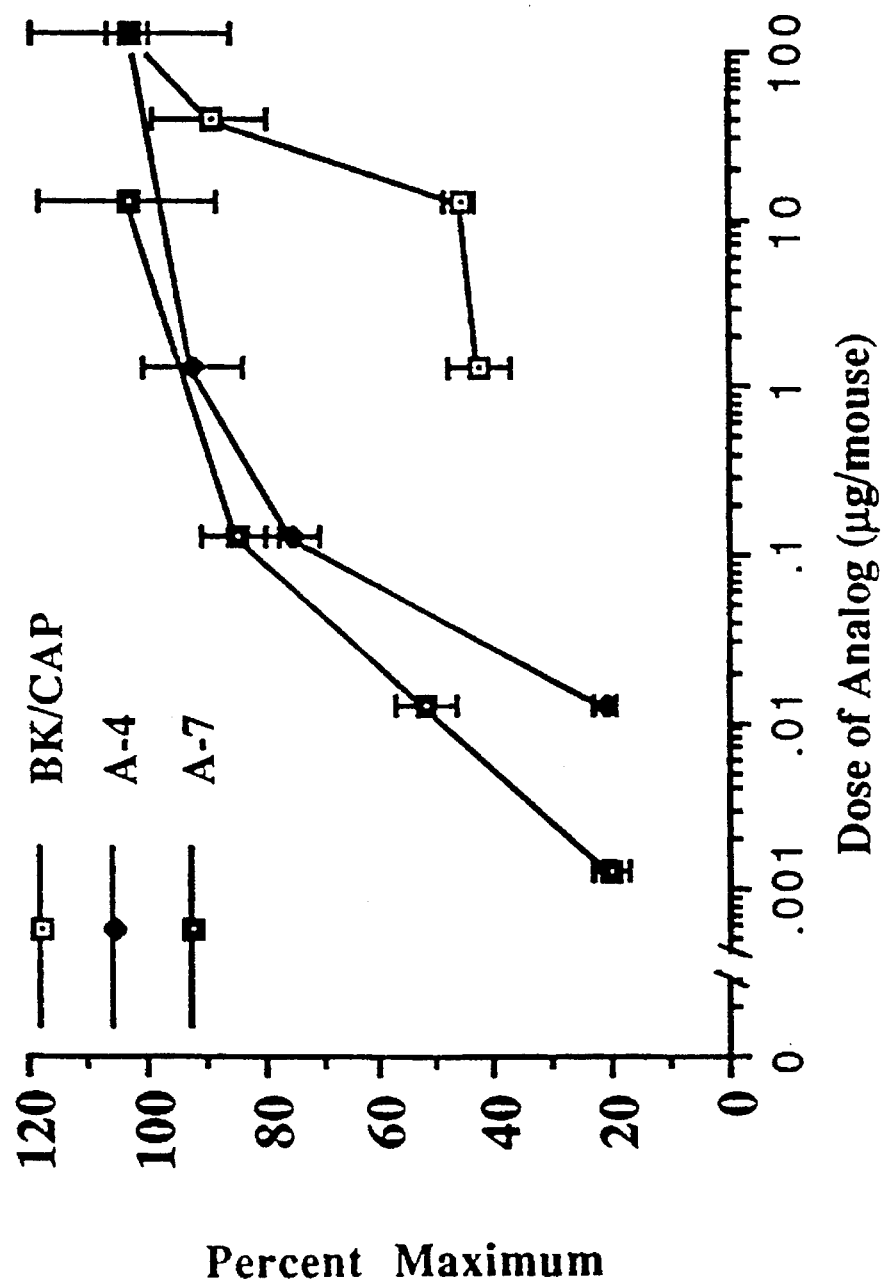
FIG. 3b is a graphic representation of brain uptake of sucrose displayed as percent of maximum uptake, following the administration of bradykinin or permeabilizer analogues.

Dose Response Relationship of Bradykinin and Other Blood-Brain Barrier Permeabilizers Sucrose Uptake Studies The methodology for these experiments is similar to the above two time course studies with the exception that all mice were killed 10 minutes after receiving a single tail vein injection of $^{14}C$-sucrose simultaneously with bradykinin or another blood-brain barrier permeabilizer. FIG. 3a shows the amount of $^{14}C$-sucrose uptake expressed as 100× percent of injected dose over various concentrations of bradykinin and the other blood-brain barrier permeabilizers after 10 minutes. FIG. 3b represents the percent maximum response (sucrose uptake) over the range of doses of bradykinin and other blood-brain barrier permeabilizers shown. The blood-brain barrier permeabilizer A-4 [Thi$^5$, Phe$^8\psi(CH_2$-NH) Arg$^9$] bradykinin, and, particularly, A-7 are more potent than the combination of bradykinin and captopril (BK+Cap). The number of mice per data point ranged from 12 to 16.

EXAMPLE V

Uptake of Substances of Different Molecular Weights Into the Brain of Mice When Co-administered With A-7

The methodology of these experiments is similar to that of the above two examples. Specific radioactively labeled molecules of different molecular weight and structure, either with saline or with 10 μg of A-7, were intravenously injected into mice via the tail vein. The animals were sacrificed 10 minutes after the coinjection and the radioactivity present in brain was measured as described previously for $^{14}C$ sucrose. The results of these studies are shown in Table I.

TABLE I

| Uptake of Radiolabelled Substances into the Brain | | | |
|---|---|---|---|
| | Mol. | 100 × % Injected Dose | |
| Molecule | Weight | Control | +10 μg A-7 |
| $^{14}C$-Sucrose | 342 | 5.9 ± 1.4 | 16.5 ± 4.9 |
| $^3H$-Inulin | 5,000 | 0.075 ± 0.018 | 0.110 ± 0.016 |

TABLE I-continued

Uptake of Radiolabelled Substances into the Brain

| Molecule | Mol. Weight | 100 × % Injected Dose Control | +10 μg A-7 |
|---|---|---|---|
| $^3$H-RNase | 12,600 | 0.123 ± 0.039 | 0.117 ± 0.030 |
| $^3$H-Myoglobin | 14,000 | 0.092 ± 0.022 | 0.073 ± 0.014 |
| $^3$H-Carbonic Anhydrase | 30,000 | 0.090 ± 0.013 | 0.106 ± 0.015 |
| $^3$H-Ovalbumin | 46,000 | 0.079 ± 0.016 | 0.093 ± 0.017 |
| $^3$H-Bovine Serum Albumin | 68,000 | 0.333 ± 0.098 | 0.209 ± 0.056 |

Data are presented as mean±s.d. for 7 to 15 mice in each group.

It appears that substances with greater molecular weights do not readily cross the blood-brain barrier when coinjected with A-7. This suggests that the blood-brain barrier permeabilizer characteristics of A-7 are restricted to lower molecular weight substances.

EXAMPLE VI

The Effect of the Anti-Neoplastic Agent Cisplatin on the Survival Time of Rats with Brain Tumor Implants When Co-administered with Bradykinin or A-7

Male Fisher 344 rats (200–250 g) were anesthetized with ketamine HCL (100 mg/kg) and acepromazine (10 mg/kg). The animals were placed in a stereotaxic device. The heads of the animals were shaved and a midline incision was made to expose the skull. A small hole was drilled over the right sensorimotor cortex. A 100 μl cell suspension (250,000 9L Glioma cells) was injected over 5 minutes into the right caudate putamen of each animal and the scalp sutured. Animals were observed daily for signs of failing health. When signs of very poor health were observed (eye hemorrhage or loss of righting reflex) animals were killed and the brains examined for presence of tumor.

On days 5 through 14, the animals received the following intravenous treatments via the tail vein: no treatment; cisplatin 200 μg/rat; A-7 50 μg and 5 minutes later cisplatin; or captopril pretreatment followed by 1 mg bradykinin 15 minutes later (BK+Cap) and cisplatin 5 minutes after the bradykinin. The results are shown in Table II as mean with range.

TABLE II

| Treatment Group | Median Survival (days) | No. Animals |
|---|---|---|
| Control | 14, Range 10–16 | 6 |
| Cisplatin | 13, Range 9–18 | 9 |
| BK + Cap + Cisplatin | 16, Range 10–21 | 9 |
| A-7 + Cisplatin | 20.5, Range 10–62 | 9 |

Figure 4:
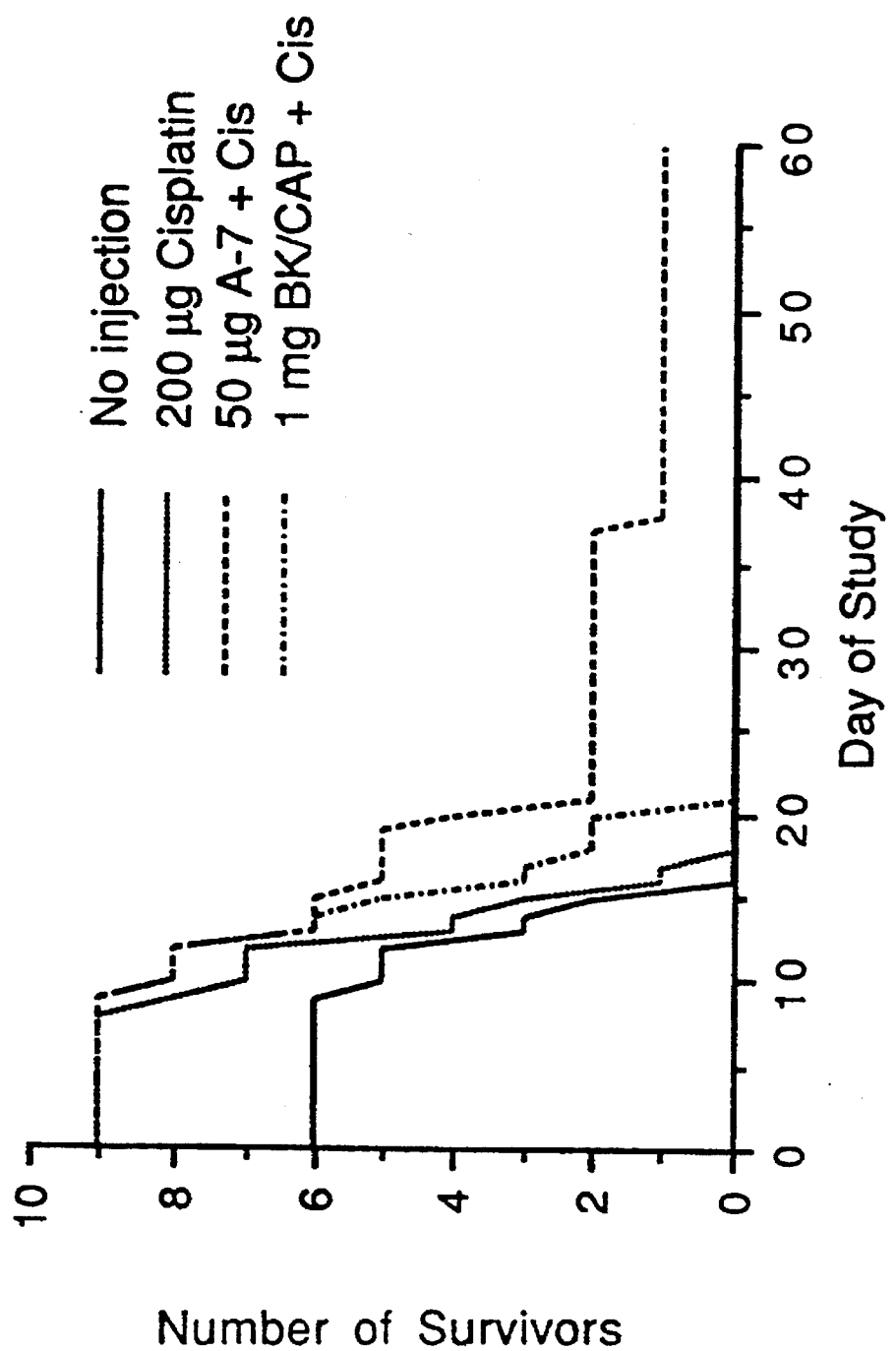
FIG. 4 is a graphic representation of the effects of no treatment; treatment with cisplatin; treatment with bradykinin, captopril and cisplatin; and treatment with a permeabilizer A-7 and cisplatin on survival time (days) of rats implanted with a brain tumor.

FIG. 4 illustrates the survival times of all animals in the study. It should be noted that 2 animals in the A-7+Cisplatin treatment group had extended survival times, with one animal dying on day 38 and the other sacrificed at day 62. Both animals had evidence of tumor growth.

Figure 5:
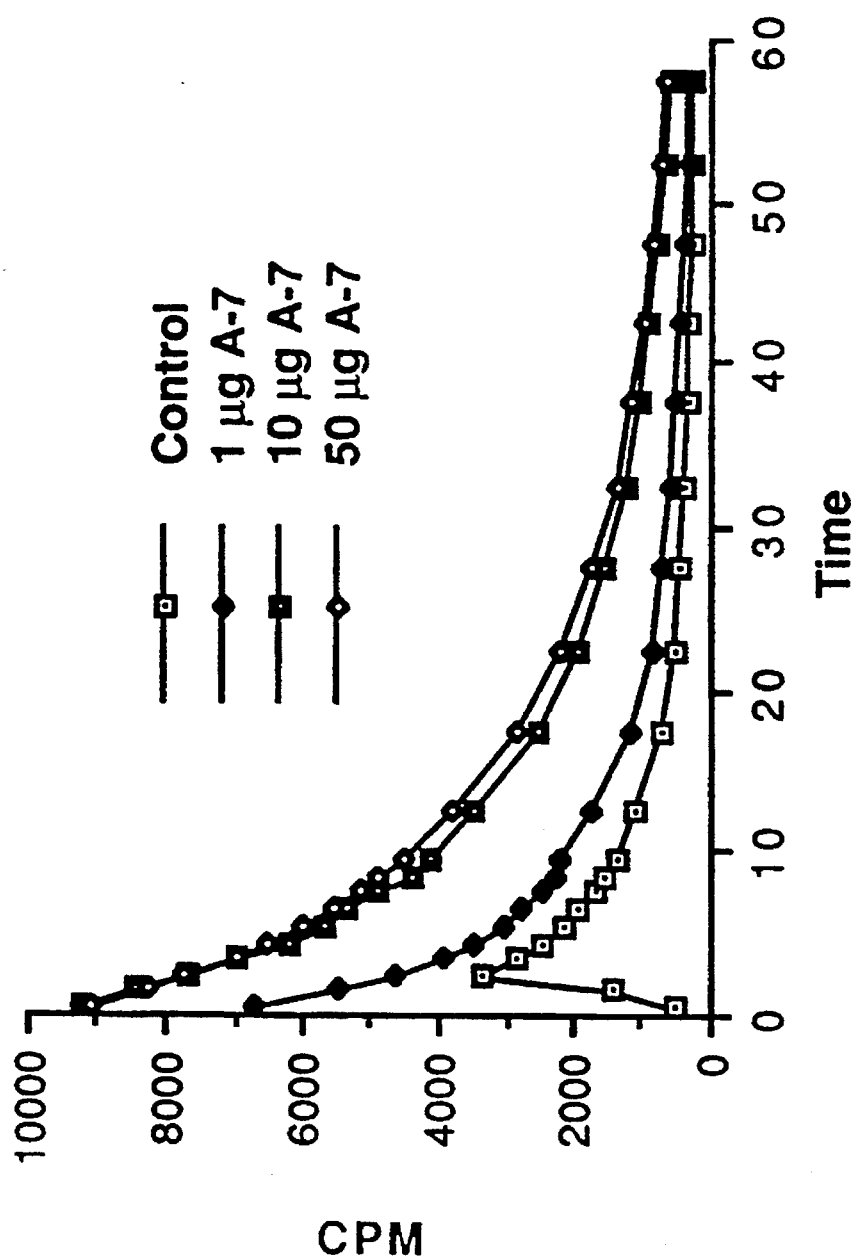
FIG. 5 is a graphic representation of the brain uptake of an imaging agent intravenously injected 3 minutes after either saline or one of three different amounts of permeabilizer A-7 was intravenously injected into rats.

EXAMPLE VII $^{99m}$Tc-DISIDA (N-[2,6-Diisopropylacetanilide]imiodiacetic Acid) Uptake Into the Head Region (Brain) in Rates Female Sprague-Dawley rats (250–300 g) were anesthetized with pentobarbital (60 mg/kg) and ketamine (100 mg/kg). The femoral veins were surgically exposed and the right vein was injected either with saline or a range of A-7 concentrations. After three minutes, a bolus of $^{99m}$Tc-DISIDA was injected into the left femoral vein. The rats were immediately placed on a gamma camera and the radioactivity counted initially at 1 minute intervals and then at 5 minute intervals for 1 hour. The head region where the brain is the primary organ was identified and the amount of radioactivity present in this region is shown in FIG. 5 for each of the concentrations of A-7 tested. The data for each concentration are radioactivity measurements from a single rat. At very early times the A-7 enhanced the uptake of $^{99m}$Tc-DISIDA into this region relative to the control animal. This experiment is representative of two similar studies.

Figure 6:
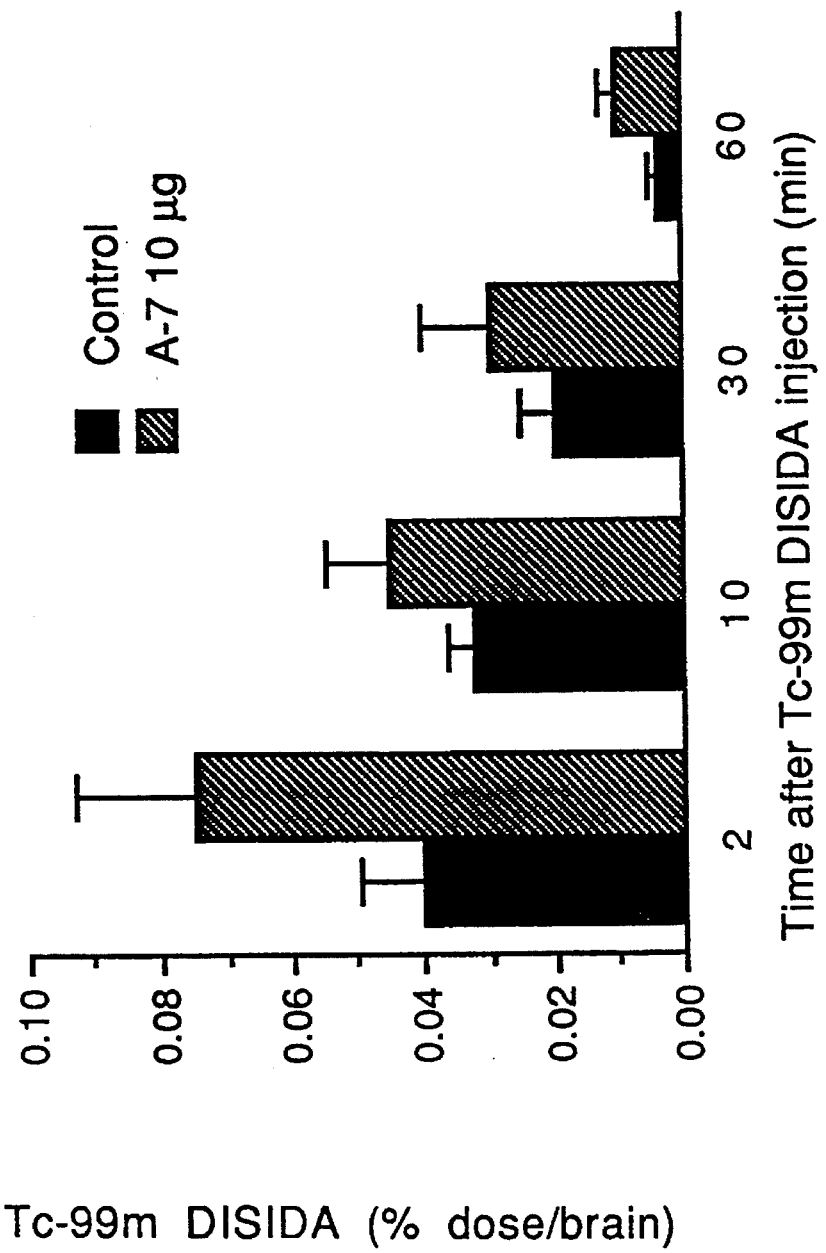
FIG. 6 is a histogram which illustrates the effect of intravenously administered permeabilizer A-7 on the uptake of the imaging agent DISIDA into the brain.

In another set of experiments, a single intravenous injection of A-7 was given into a femoral vein of an anesthetized rat. Two minutes later, an injection of $^{99m}$Tc-DISIDA was given into the contralateral femoral vein. In control animals, no A-7 was injected (sham injection). At time intervals of 2, 10, 30 or 60 minutes after the $^{99m}$Tc-DISIDA injection, the rats were sacrificed, their brains removed and counted in a gamma counter. The brain uptake of Tc-DISIDA was calculated and expressed as percent of injected dose per organ. The biodistribution of $^{99m}$Tc-DISIDA in the whole brain of untreated and A-7 treated rats at selected times post-injection is shown in Table III and FIG. 6.

TABLE III

Biodistribution of $^{99m}$Tc-DISIDA in Brain

| Time (after $^{99m}$Tc-DISIDA Injection) | % Injected Dose/Brain Control | +10 μg RMP-7 |
|---|---|---|
| 2 min. | 0.040 ± 0.013 | 0.075 ± 0.019 |
| 5 min. | 0.032 ± 0.003 | 0.046 ± 0.006 |
| 10 min. | 0.022 ± 0.005 | 0.028 ± 0.003 |
| 60 min. | 0.004 ± 0.001 | 0.010 ± 0.003 |

The data are expressed as mean±s.d. for three animals per group.

These results demonstrate that larger amounts of $^{99m}$Tc-DISIDA are found in the brain of A-7 treated rates when compared to control rats at early times post-injection of the labeled agent.

EXAMPLE VIII

The Effect of A-7 on the Brain Uptake and Antinociceptive Effect of Loperamide. Tail Flick Assay Female Balb/C mice weighing approximately 20 g were used. The tail flick assay was performed using a Tail flick Apparatus model TF6 (Emdie Instruments, Maidens, Va.). The intensity of the heat source was adjusted daily to yield a reaction time between 2.0 and 3.2 seconds in naive untreated mice. The maximum time of exposure to the heat source allowed was 7.5 seconds. The tail withdrawal reaction time of mice was measured 4 times at 10 second intervals. immediately prior to intravenous injections via the tail vein. The last three values were averaged and taken as baseline value ($V_o$). Another set of measurements was taken at the following intervals after tail vein injection of the opiate receptor agonist loperamide and other agents: immediately, 5 min, 10 min, 15 min, 30 min, and 60 min. The last three values for each of these time points (V) were averaged. In some experiments the opiate receptor antagonist naloxone (10 mg/kg; 100 μl in saline) was administered intraperitoneally 15 minutes prior to administration of A-7 (0.1 μg) and loperamide (25 μg). The results were expressed as percent antinociceptive response according to the formula: $100 \times (V - V_o)/(7.5 - V_0 o$.

Figure 7:
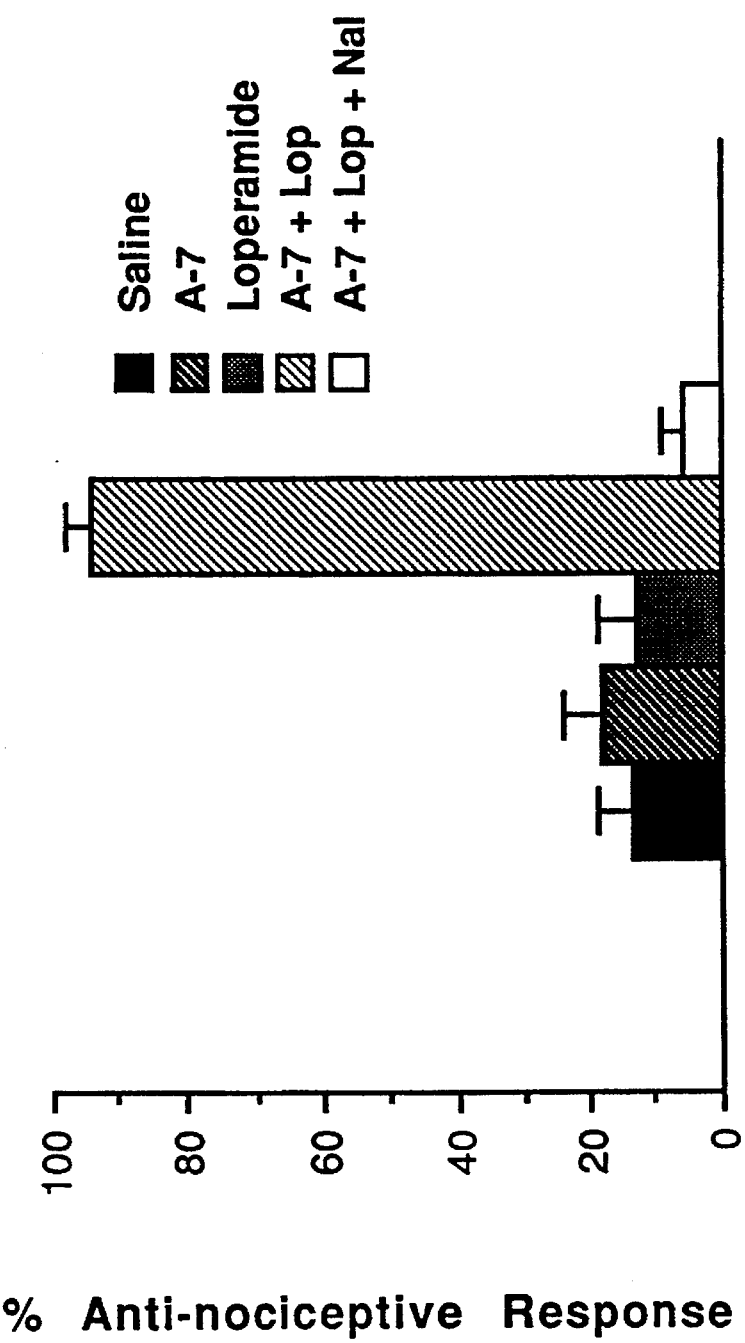
FIG. 7 is a histogram which illustrates the effect of a co-administered permeabilizer A-7 on the antinociceptive activity of loperamide in the mouse tail flick assay enously injected into rats.

FIG. 7 illustrates the ability of A-7 to enhance the permeability of the blood-brain barrier to loperamide as evidenced by the increase in % antinociceptive response. Each point represents pooled data from 2 experiments with 4 mice (total of 8 mice) 30 minutes after injection of loperamide, A-7, and A-7 and loperamide with or without naloxone pretreatment. A complete antinociceptive response was obtained when A-7 was coinjected with loperamide. The effect was completely antagonized by pretreatment with naloxone.

EXAMPLE IX

The Effect of a Dopaminergic Antagonist When Co-administered with A-7 on the Locomotor Activity of Rats Domperidone is a dopamine receptor antagonist used clinically as an anti-emetic by virtue of its action at the area postrema outside the blood-brain barrier. Reports in the literature demonstrated that domperidone does not cross the blood-brain barrier but when given as an injection into the cerebral ventricles, it effectively blocks binding of dopaminergic compounds, such as apomorphine, to dopamine receptors. A pertinent test is whether domperidone can antagonize a dopamine receptor agonist-induced increase in motor activity when co-administered with A-7 but is ineffective when administered without A-7.

Sprague-Dawley rats (125–150 g) were habituated for two days to activity cages. The activity cages were standard size rat cages with two photocell beams running across the floor of each cage. Any movement of the rat through either of the beams was recorded by a computer. Locomotor activity was measured as the number of beam breaks in a sequence of 10-minute intervals over a two hour period.

The rats were given a coinjection of 10 μg A-7 and 300 μg domperidone, or the domperidone alone, one hour before a subcutaneous injection of apomorphine (0.75 mg/kg), which is a dopamine agonist. The motor activity of the rats was measured in activity cages over 10-minute intervals for up to 2 hours postapomorphine injection.

Figure 8:
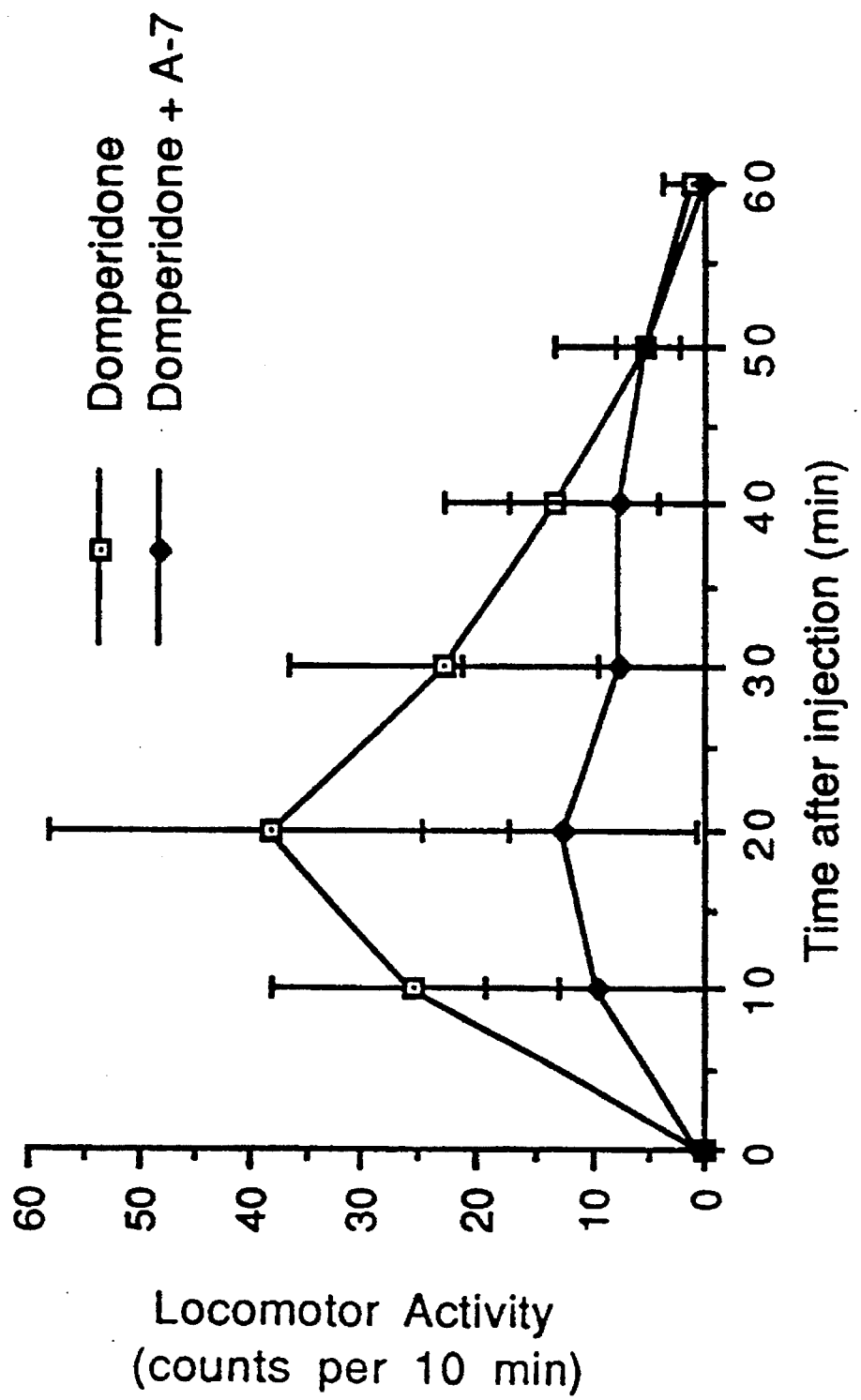
FIG. 8 is a graphic representation of the effects of a dopamine receptor antagonist (domperidone) co-administered with permeabilizer A-7 on apomorphine-induced motor activity of rats.

The results of this experiment with 3 rats in each treatment group are shown in FIG. 8. The combination of A-7 and domperidone antagonized the increase in motor activity associated with apomorphine. Domperidone alone had little, if any, effect on motor activity induced by apomorphine which readily crosses the blood-brain barrier.

EXAMPLE X

The Effect of Angiotensin II When Co-Administered With A-7 on the Drinking Behavior of Rats Angiotensin II in supra-physiological concentrations has been shown to induce drinking behavior in water satiated rats. This behavior has been suggested to occur as a result of stimulation of angiotensin II receptors within areas of the brain not associated with the cerebroventricular organs. Studies were performed to evaluate the effect of co-administration of A-7 with an angiotensin II analogue that is capable of causing drinking behavior when administered at a high dose.

Rats were given a coinjection of 10 μg A-7 and either 0.1, 0.3, 3, 10 or 30 μg of β-angiotensin II, or the β-angiotensin II, alone, via tail vein injection. The volume of water consumed by each rat over a 1 hour interval was measured.

Figure 9:
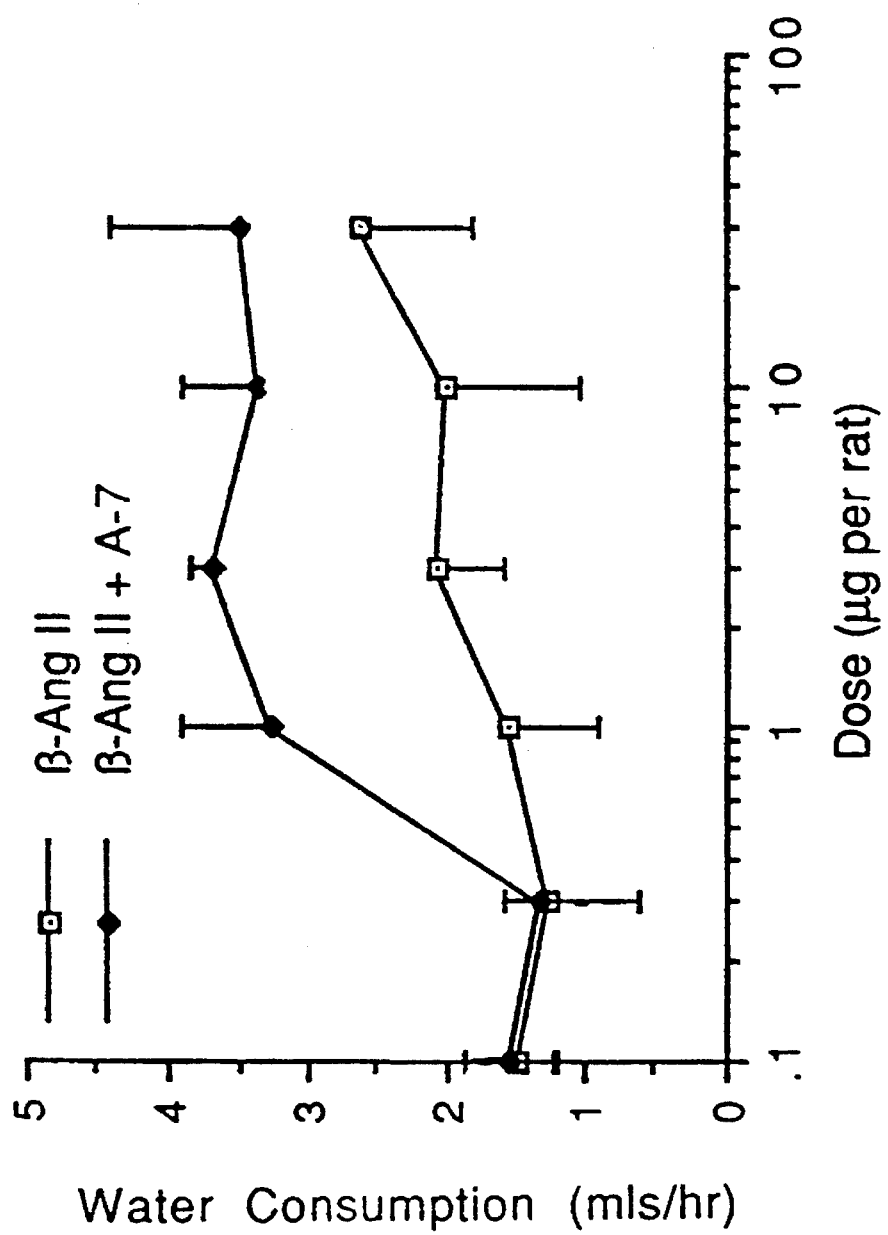
FIG. 9 is a graphic representation of the effects of an angiotensin II analogue co-administered with permeabilizer A-7 on drinking behavior in rats.

The results of this study with 6 rats in each dosage group are shown in FIG. 9. Co-administration of A-7 and the angiotensin II analogue caused the dose response curve to shift to the left, or toward lower doses of analogue, when compared to administration of the analogue alone.

In another study, rats were given either saline, 1 μg of β-angiotensin II, 1 μg of β-angiotensin II and 10 μg of A-7, 1 μg of β-angiotensin II and 8 μg of saralasin or 1 μg of β-angiotensin II plus 10 μg of A-7 plus 8 μg of saralasin via tail vein injection. The saralasin was given because it is a known angiotensin II receptor antagonist. Again, the volume of water consumed by each rat over a 1 hour interval was measured.

Figure 10:
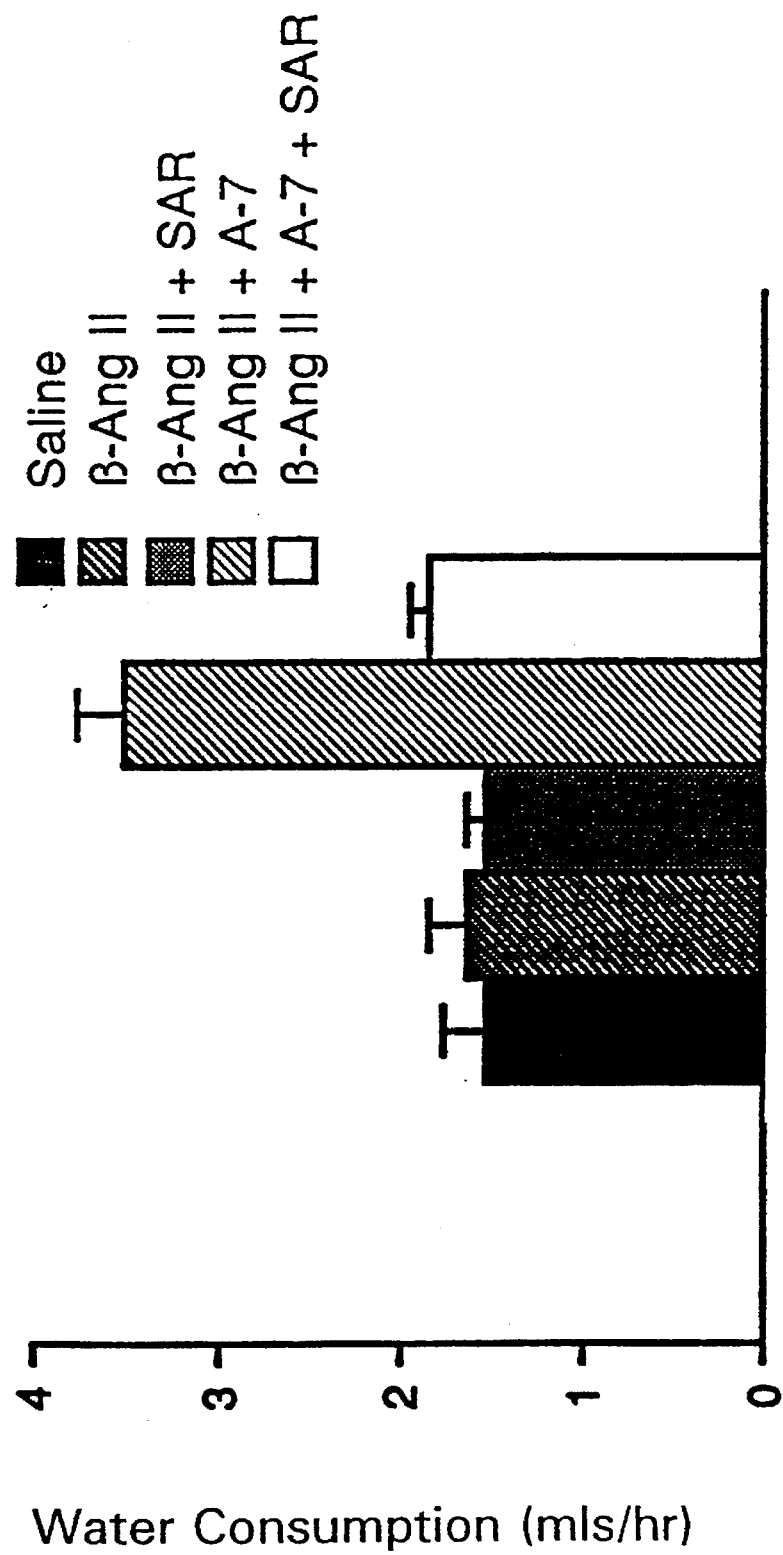
FIG. 10 is a histogram which illustrates the effects of an angiotensin II analogue and inhibitor co-administered with permeabilizer A-7 on drinking behavior in rats.

The results of this study with 3 rats in each group are shown in FIG. 10. The co-administration of A-7 and β-angiotensin II caused a significant increase in water consumption compared to the angiotensin II analogue alone or together with saralasin. When saralasin is co-administered with A-7 and the analogue, the water consumption remains within a normal range which indicates an inhibition of angiotensin II analogue-induced drinking behavior by the addition of the angiotensin II receptor antagonist.

EQUIVALENTS

Those skilled in the art will recognize, or be able to ascertain using no more than routine experimentation, many equivalents to the specific embodiment of the invention described specifically herein. Such equivalents are intended to be encompassed in the scope of the following claims.

---

We claim:

1. A blood-brain barrier permeabilizing peptide having the amino acid sequence of H-arginine-proline-hydroxyproline-glycine-thienylalanine-serineproline-(4-Me-tyrosine)ψ(CH$_2$NH)-arginine-OH (SEQ ID NO: 1) or a conformational analogue thereof which is said peptide with at least one of the following modifications:

a) the N-terminal arginine is replaced by an amino acid analogue containing a guanidino side chain;

b) the second amino acid (proline) is replaced by hydroxyproline, dehydroproline or N-methylalanine;

c) the third amino acid (hydroxyproline) is replaced by proline, dehydroproline, alanine or N-methylalanine;

d) the fifth amino acid (thienylalanine) is replaced by another aromatic amino acid or a hydrophobic aliphatic amino acid;

e) the sixth amino acid (serine) is replaced by glycine or alanine;

f) the seventh amino acid (proline) is replaced by hydroxyproline, dehydroproline or N-methylalanine; and g) the C-terminal arginine is replaced by an amino acid analogue containing a guanidino side chain the C-terminal arginine is replaced by an amino acid analogue containing a guanidino side chain; and b. a pharmaceutically acceptable carrier.

2. A pharmaceutical composition for administration to an animal to increase the permeability of the blood-brain barrier to a molecule, comprising:
   a) an effective amount of a peptide with the amino acid sequence of H-arginine-proline-hydroxyproline-glycine-thienylalanine-serine-proline-4--Me-tyrosine)ψ(CH$_2$NH)-arginine-OH (SEQ ID NO: 1) or a conformational analogue thereof which is said peptide with at least one of the following modifications:
   i) the N-terminal arginine is replaced by an amino acid analogue containing a guanidino side chain;
   ii) the second amino acid (proline) is replaced by hydroxyproline, dehydroproline or N-methylalanine;
   iii) the third amino acid (hydroxyproline) is replaced by proline, dehydroproline, alanine or N-methylalanine;
   iv) the fifth amino acid (thienylalanine) is replaced by another aromatic amino acid or a hydrophobic aliphatic amino acid;
   v) the sixth amino acid (serine) is replaced by glycine or alanine;
   vi) the seventh amino acid (proline) is replaced by hydroxyproline, dehydroproline or N-methylalanine; and
   vii) the eighth amino acid (4-Me-tyrosine) is replaced by another O-alkyl tyrosine or a hydrophobic aliphatic amino acid.

3. The blood-brain barrier permeabilizing peptide of claim 1 wherein said modification is chosen from:
   a) β-cycloarginine, homoarginine, γ-hydroxyarginine, canavanine, N$^ω$-amidinocitrulline, 2-amino-4-guanidobutanoic acid for the N-terminal or C-terminal arginine;
   b) hydroxyproline or dehydroproline for the second or seventh amino acids (proline);
   c) proline or dehydroproline for the third amino acid (hydroxyproline);
   d) dehydrophenylalanine, phenylalanine or another aromatic analogue for the fifth amino acid (thienylalanine); and
   e) glycine for the sixth amino acid (serine).

4. The blood-brain barrier permeabilizing peptide of claim 1 wherein all optically active amino acids are of the L-configuration.

* * * * *

UNITED STATES PATENT AND TRADEMARK OFFICE
CERTIFICATE OF CORRECTION

PATENT NO. : 5,506,206
DATED : April 9, 1996
INVENTOR(S) : John W. Kozarich, Gary F. Musso and Bernard Malfroy-Camine It is certified that error appears in the above-indentified patent and that said Letters Patent is hereby corrected as shown below:

In Column 18, line 64:
    delete "the C-terminal arginine is replaced by an amino acid analogue containing a guanidino side chain; and
    b. a pharmaceutically acceptable carrier."

In Column 20, line 1: after "vii)", delete
    "the eighth amino acid (4-Me-tyrosine) is replaced by another O-alkyl tyrosine or a hydrophobic aliphatic amino acid"

and insert therefor --the C-terminal arginine is replaced by an amino acid analogue containing a guanidino side chain; and
b] a pharmaceutically acceptable carrier--.

Signed and Sealed this

Sixth Day of August, 1996

Attest:

BRUCE LEHMAN

Attesting Officer     Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide

```
(  i  i  i  ) HYPOTHETICAL: NO (  v  i  ) ORIGINAL SOURCE:
            ( C ) INDIVIDUAL ISOLATE: Synthesized (  i  x  ) FEATURE:
            ( A ) NAME/KEY: Modified-site
            ( B ) LOCATION: 3
            ( D ) OTHER INFORMATION: /label=other
                    / note="hydroxyproline"

(  i  x  ) FEATURE:
            ( A ) NAME/KEY: Modified-site
            ( B ) LOCATION: 5
            ( D ) OTHER INFORMATION: /label=other
                    / note="thienylalanine"

(  i  x  ) FEATURE:
            ( A ) NAME/KEY: Modified-site
            ( B ) LOCATION: 8
            ( D ) OTHER INFORMATION: /label=other
                    / note="substituent is a 4-methyl group"

(  i  x  ) FEATURE:
            ( A ) NAME/KEY: Modified-site
            ( B ) LOCATION: 8..9
            ( D ) OTHER INFORMATION: /label=other
                    / note="reduced peptide bond"

(  x  i  ) SEQUENCE DESCRIPTION: SEQ ID NO:1:

Arg   Pro   Xaa   Gly   Xaa   Ser   Pro   Tyr   Arg
    1                       5

(  2  ) INFORMATION FOR SEQ ID NO:2:

(  i  ) SEQUENCE CHARACTERISTICS:
            ( A ) LENGTH: 9 amino acids
            ( B ) TYPE: amino acid
            ( D ) TOPOLOGY: linear (  i  i  ) MOLECULE TYPE: peptide (  i  i  i  ) HYPOTHETICAL: NO (  x  ) PUBLICATION INFORMATION:
            ( A ) AUTHORS: Marceau,
                    et al.,
            ( B ) TITLE: Pharmacology of Kinins: Their Relevance to
                    Tissue Injury and Inflammation
            ( C ) JOURNAL: General Pharmacology
            ( D ) VOLUME: 14
            ( E ) ISSUE: 2
            ( F ) PAGES: 209-229
            ( G ) DATE: 1983

(  x  i  ) SEQUENCE DESCRIPTION: SEQ ID NO:2:

Arg   Pro   Pro   Gly   Phe   Ser   Pro   Phe   Arg
    1                       5
```